United States Patent
Shibata et al.

(10) Patent No.: US 8,308,721 B2
(45) Date of Patent: Nov. 13, 2012

(54) SURGICAL SYSTEM AND SURGICAL METHOD

(75) Inventors: Norikiyo Shibata, Yamato (JP); Sadayoshi Takami, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 953 days.

(21) Appl. No.: 12/327,982

(22) Filed: Dec. 4, 2008

(65) Prior Publication Data
US 2010/0145332 A1   Jun. 10, 2010

(51) Int. Cl.
*A61B 18/18* (2006.01)
(52) U.S. Cl. ......................................................... 606/38
(58) Field of Classification Search ............... 606/34–40
See application file for complete search history.

(56) References Cited

U.S. PATENT DOCUMENTS

| | | | |
|---|---|---|---|
| 4,727,874 | A | 3/1988 | Bowers et al. |
| 6,039,732 | A | 3/2000 | Ichikawa et al. |
| 6,547,786 | B1 | 4/2003 | Goble |
| 2002/0082593 | A1 | 6/2002 | Hareyama et al. |
| 2008/0208108 | A1 | 8/2008 | Kimura |

FOREIGN PATENT DOCUMENTS

| | | |
|---|---|---|
| EP | 1 053 719 A1 | 11/2000 |
| EP | 1 964 530 A1 | 9/2008 |
| GB | 2 164 473 A | 3/1986 |
| JP | 61-124266 | 6/1986 |
| JP | 8-50646 | 5/1996 |
| JP | 08-308854 | 11/1996 |
| JP | 2000-041994 | 2/2000 |
| JP | 2000-342599 | 12/2000 |
| JP | 2000-350732 | 12/2000 |
| JP | 2001-520081 | 10/2001 |
| JP | 2002-238916 | 8/2002 |
| JP | 2002-306507 | 10/2002 |
| JP | 2007-143878 | 6/2007 |
| JP | 2008-212679 | 9/2008 |
| WO | WO 94/23659 | 10/1994 |
| WO | WO 99/20213 | 4/1999 |

OTHER PUBLICATIONS

International Search Report dated Dec. 22, 2009.

*Primary Examiner* — Nicholas Lucchesi
*Assistant Examiner* — Nathan R Price
(74) *Attorney, Agent, or Firm* — Scully, Scott, Murphy & Presser, PC

(57) ABSTRACT

A surgical system includes: a treatment portion for treating living body tissue targeted for treatment; an ultrasound supplying section for supplying ultrasound via ultrasound transducers which produce ultrasound vibration; a radio-frequency electrical power supplying section for supplying, to the treatment portion, radio-frequency electrical power having an output wave-form defined by a base frequency and a repetition frequency; and a controlling section for controlling at least one of a voltage root-mean-square value and a crest factor, so that the voltage peak value of the output wave-form of the radio-frequency electrical power does not exceed a fixed value.

13 Claims, 14 Drawing Sheets

SURGICAL SYSTEM AND SURGICAL METHOD

BACKGROUND OF THE INVENTION

1. Field of the Invention

The present invention relates to surgical system and a surgical method for performing surgery using ultrasound vibration energy and radio-frequency electrical energy.

2. Description of the Related Art

In surgical techniques of recent years, ultrasound driving apparatus capable of performing dissection treatments while coagulating the organ or living body tissue targeted in the surgery using ultrasound vibration energy and radio-frequency ablation apparatus (radio-frequency electrical power supplying apparatus or electric scalpel apparatus) for passing radio-frequency electrical energy through living body tissue to perform ablation have been widely used.

For instance, Japanese Patent Application Laid-Open Publication No. 8-50646 discloses an electric scalpel apparatus in which voltage, current, power, load impedance, and crest factor are measured and operating parameters such as the peak-to-peak voltage are controlled.

Further, Japanese Patent Application Laid-Open Publication No. 2007-143878 discloses a radio-frequency power source and a radio-frequency surgical apparatus in which control is performed by detecting an increase in impedance from a first impedance and outputting a radio-frequency current and a radio-frequency voltage having a second wave-form of a lower crest factor than a first wave-form.

Further, Japanese Patent Application Laid-Open Publication No. 6-292685 discloses an apparatus which simultaneously outputs ultrasound and radio-frequency waves.

By applying ultrasound vibration energy and radio-frequency electrical energy simultaneously to living body tissue targeted for treatment target via a treatment portion, it is possible to reduce sticking of the living body tissue to the treatment portion and achieve smooth dissection of the living body tissue.

It is well-known that when ultrasound vibration is applied to living body tissue, a portion of the tissue scatters to form a mist-like state.

However, when the treatment target is living body tissue which includes a high proportion of fat, the fat scatters to form a mist while the treatment is performed, and in rare cases the radio-frequency electrical energy ignites the fat in the mist-like state, causing flames.

Hence, preventing such ignitions makes it easier to perform the treatment smoothly.

SUMMARY OF THE INVENTION

A surgical system of the invention includes: a treatment portion for treating living body tissue targeted for treatment; an ultrasound supplying section for supplying ultrasound oscillation to the treatment portion via ultrasound transducers which produce ultrasound vibration; a radio-frequency electrical power supplying section for supplying, to the treatment portion, radio-frequency electrical power having an output wave-form defined by a base frequency and a repetition frequency; and a controlling section for controlling at least one of a voltage root-mean-square value and a crest factor, which is calculated by dividing a voltage peak value by the voltage root-mean-square value, so that the voltage peak value at peaks in the output wave-form of radio-frequency electrical power does not exceed a predetermined value, when the ultrasound oscillation and the radio-frequency electrical power are simultaneously output from the ultrasound supplying section and the radio-frequency electrical power supplying section to the treatment portion.

A surgical method of the invention for performing surgery using a treatment instrument on living body tissue targeted for treatment includes: a simultaneous supplying step of simultaneously supplying, to a treatment portion at a distal end of the treatment instrument, ultrasound oscillation via ultrasound transducers and radio-frequency electrical power having an output wave-form defined by a base frequency and a repetition frequency; and a controlling step of controlling, based on a judgment result of the impedance value detected in the judging step being in the predetermined range, at least one of a voltage root-mean-square value and a crest factor, which is calculated by dividing a voltage peak value by the voltage root-mean-square value, so that the voltage peak value at peaks in the output wave-form of the radio-frequency electrical power does not exceed a predetermined value, when the ultrasound oscillation and the radio-frequency electrical power are simultaneously output to the treatment portion by the simultaneous supplying step.

DETAILED DESCRIPTION OF THE PREFERRED EMBODIMENTS

The following describes embodiments of the invention with reference to the drawings.

First Embodiment

FIGS. 1 to 9 are for explaining a first embodiment of the invention.

Figure 1:
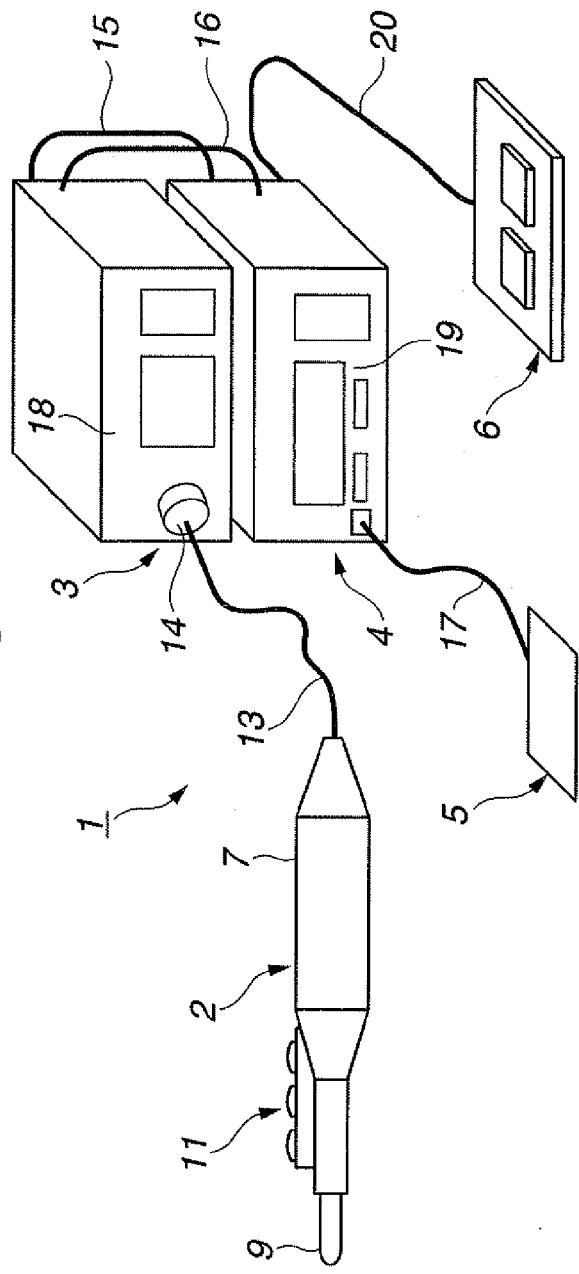
FIG. 1 is a perspective view showing an overall configuration of an ultrasound and radio-frequency wave surgical system of a first embodiment of the invention.

FIG. 1 shows an overall configuration of an ultrasound and radio-frequency wave surgical system 1 of the first embodiment of the invention. The ultrasound and radio-frequency wave surgical system 1 includes a hand-piece 2 which is a treatment instrument for performing treatments such as coagulating dissection and the like on living body tissue by supplying ultrasound vibration energy and radio-frequency electrical energy (hereinafter abbreviated to "ultrasound" and "radio-frequency waves") to the tissue targeted for treatment.

The ultrasound and radio-frequency wave surgical system 1 includes an ultrasound driving apparatus (hereinafter abbreviated to ultrasound generator) 3 which supplies an ultrasound drive signal to drive an ultrasound transducer 23 (see FIG. 2) built into the hand-piece 2, and a radio-frequency electrical power outputting apparatus (hereinafter abbreviated to radio-frequency wave generator) 4 which supplies radio-frequency electrical power (radio-frequency current) to the hand-piece 2.

The ultrasound and radio-frequency wave surgical system 1 includes a foot-switch 6 for performing an instruction operation to switch the supply of radio-frequency electrical power on and off and an opposing electrode plates 5 to form a return circuit of the radio-frequency electrical power.

The hand-piece 2 includes a grasping section 7 which is grasped by an operator and a probe 8 protruding ahead from the grasping section 7. A treatment portion 9 for performing treatments such as coagulating dissection and the like is provided at a distal end of the probe 8.

A hand-switch unit (hereinafter abbreviated to hand-switch) 11 for making selections during treatment using the treatment portion 9 is provided on the grasping section 7. The hand-switch 11 includes a dissection selection switch 12a, a coagulation selection switch 12b and a simultaneous output switch 12c for simultaneously outputting ultrasound and radio-frequency waves.

A signal cable 13 extends from a rear-end side of the grasping section 7 of the hand-piece 2, and a connector 14 at an end portion of the signal cable 13 is removably connected to a receptacle of the ultrasound generator 3.

The ultrasound generator 3 and the radio-frequency wave generator 4 are connected by a communication cable 15 to enable the transmission and reception of signals. Further, the ultrasound generator 3 and the radio-frequency wave generator 4 are connected by a radio-frequency wave cable 16.

Radio-frequency waves generated by the radio-frequency wave generator 4 are transmitted to the side of the ultrasound generator 3 via the radio-frequency wave cable 16, and the radio-frequency electrical power (radio-frequency current) is supplied to the hand-piece 2 via the connector 14 and the signal cable 13.

An end portion of an opposing electrode plate cable 17, which connects to an opposing electrode plate 5, is removably connected to the radio-frequency wave generator 4. The opposing electrode plate 5 is arranged so as to contact the buttocks or another portion of the patient over a wide area.

The ultrasound generator 3 and the radio-frequency wave generator 4 are respectively provided with front panels 18 and 19 on the front sides thereof for displaying the various operations and the like.

Note that the foot-switch 6 is connected to the radio-frequency wave generator 4 by a foot-switch cable 20.

Figure 2:
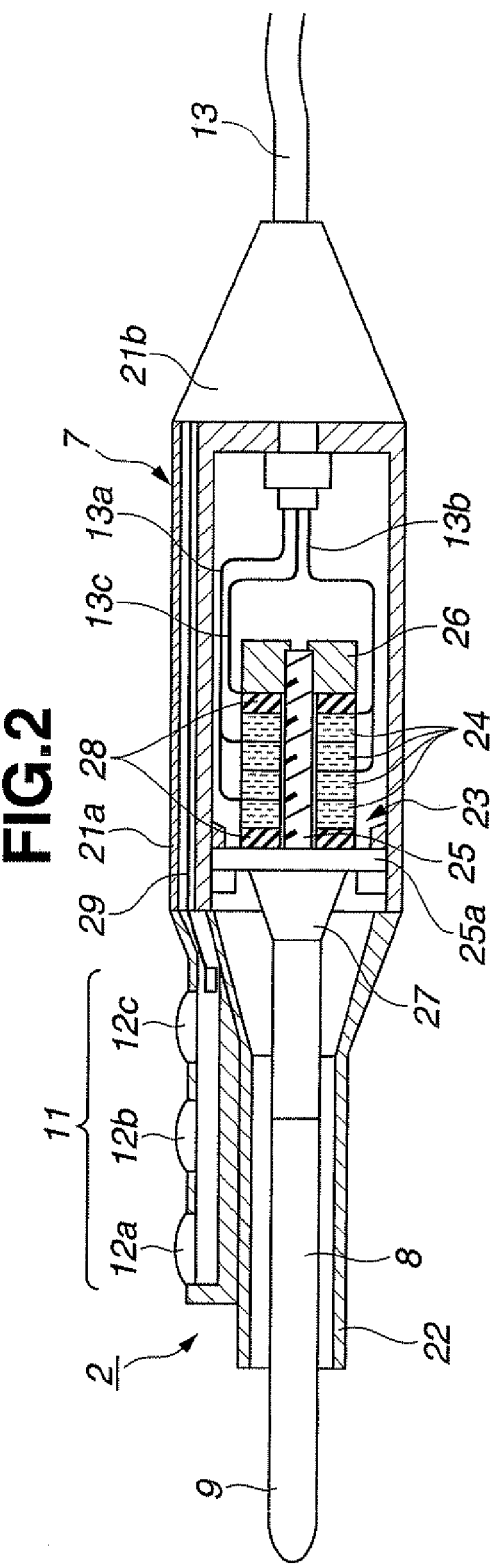
FIG. 2 is a cross-sectional view showing an internal configuration of a hand-piece.

FIG. 2 shows the internal configuration of the hand-piece 2. The hand-piece 2 includes a substantially cylindrical main case 21a which forms the grasping section 7, and a sheath 22 is linked at the front end of the main case 21a. A terminal side of the signal cable 13 is fed into the main case 21a from a rear end portion 21b. An ultrasound transducer 23 is provided in the main case 21a as ultrasound generating means, and is connected to leads 13a and 13b which transmit an ultrasound drive signal.

The ultrasound transducer 23 has a multi-layer construction including a plurality of ring-like piezoelectric devices 24. The piezoelectric devices 24 in the multilayer construction are fixed by tightening a nut 26 and a bolt 25. The plurality of piezoelectric devices 24 are caused to vibrate to produce ultrasound by applying ultrasound drive signals to electrodes provided on respective surfaces of each piezoelectric device 24 via the leads 13a and 13b. The ultrasound vibration is magnified by a horn 27 formed by a flange portion 25a at a front end of the bolt 25, and transmitted through the probe 8 to a distal end of the treatment portion 9.

Thus, ultrasound vibration energy is applied to the treatment portion 9 via ultrasound transducer 23 by applying the ultrasound drive signal from the ultrasound generator 3 to the ultrasound transducer 23. In other words, the ultrasound generator 3 and the ultrasound transducer 23 form an ultrasound supplying section which supplies ultrasound to the treatment portion 9.

The operator can perform treatment such as coagulating dissection and the like by contacting vibrating treatment portion 9 against the region targeted for treatment with friction heating caused by the ultrasound vibrations.

Note that the plurality of piezoelectric devices 24 are provided between insulating plates 28.

The nut 26, which is made of metal, forms a conducting portion that is connected to a radio-frequency output lead 13c of the signal cable 13. Then, when a radio-frequency output signal is applied to the nut 26, the signal is transmitted to the distal end of the treatment portion 9 via the metal bolt 25 and the metal probe 8.

By contacting the treatment portion 9 against the region targeted for treatment, the operator is able to cause a high-density radio-frequency current, which is radio-frequency electrical energy, to flow in the region of contact and achieve ablation. The radio-frequency current then returns to the radio-frequency wave generator 4 through the opposing electrode plate 5 and the opposing electrode plate cable 17 which form a return path.

Note that the probe 8 of the type shown in FIG. 2 passes through the metal sheath 22 which is covered by an insulation pipe not shown in the drawings.

Note that a hand-switch cable 29 which passes through the signal cable 13 includes a plurality of signal cables which connect respectively to the dissection selection switch 12a, the coagulation selection switch 12b, and the simultaneous output switch 12c. Note that the dissection selection switch 12a, the coagulation selection switch 12b, and the simultaneous output switch 12c are covered by a rubber cover portion. Each switch can be switched on and off by pressing on the rubber cover portion.

Figure 3:
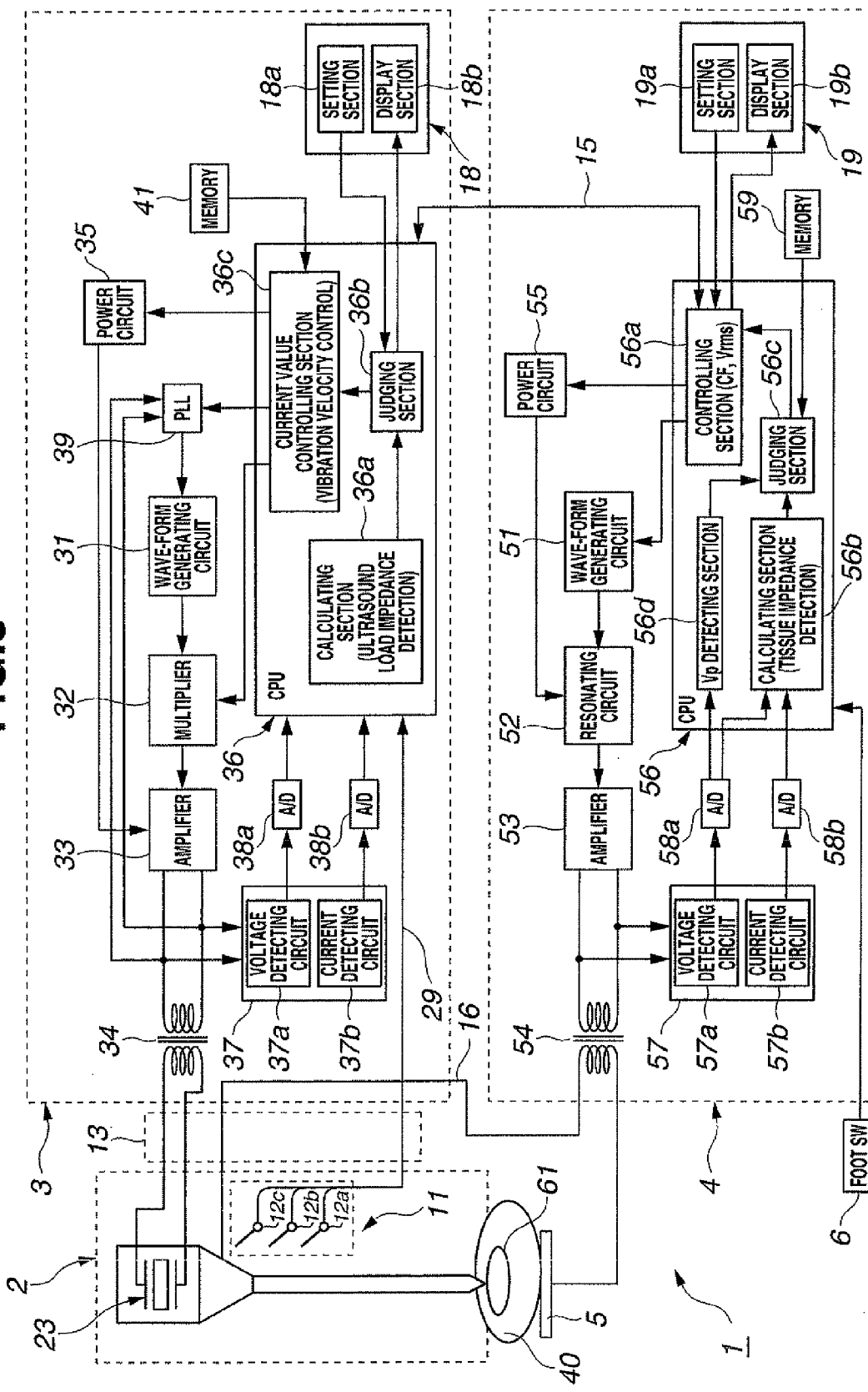
FIG. 3 is a block diagram showing a detailed configuration of the ultrasound and radio-frequency wave surgical system.

FIG. 3 shows a detailed configuration of the ultrasound generator 3 and the radio-frequency wave generator 4 shown in FIG. 1. The ultrasound generator 3 includes a wave-form generating circuit 31 which generates, for instance, a sinusoidal signal.

The sinusoidal signal outputted from the wave-form generating circuit 31 is controlled to fixed current using a multiplier 32, amplified by an amplifier 33 and then applied to a primary coil side of an output transformer 34. The sinusoidal signal is then applied to the ultrasound transducer 23 in the hand-piece 2 as the ultrasound drive signal from output terminals of a secondary coil side of the output transformer 34.

The amplitude of the ultrasound drive signal, which is to say the ultrasound output of the ultrasound transducer 23, is adjusted according to the values of a current and voltage supplied to the amplifier 33 from a power circuit 35. More specifically, the ultrasound output is controlled by a central processing unit (CPU) 36 which controls the current and voltage to appropriate level using fixed current control that described in a later section.

An ultrasound output setting value is inputted to the CPU 36 by a setting section 18a of the front panel 18.

A display section 18b which displays information such as the ultrasound output outputted from the CPU 36 is provided in the front panel 18.

After amplification by the amplifier 33, the sinusoidal signal is inputted to a voltage detecting circuit 37a and a current detecting circuit 37b which form a detecting section 37 and voltage and current of the sinusoidal signal are detected (measured). The detected voltage and current are converted to digital values by A/D converters 38a and 38b, and inputted to a calculating section 36a of the CPU 36. The sinusoidal signal amplified by the amplifier 33 is also inputted to a PLL circuit 39.

The PLL circuit 39 performs PLL control so that the ultrasound transducer 23 is driven with an ultrasound drive signal corresponding to a resonant frequency of the ultrasound transducer 23. The PLL circuit further performs control so that phases of the voltage and the current match in the ultrasound drive signal. The operation of the PLL circuit 39 is controlled by the CPU 36.

The CPU 36 includes a calculating section 36a function for calculating an ultrasound output value using voltage and current inputted via the A/D converters 38a and 38b.

The CPU 36 further includes a judging section 36b function for judging whether or not the ultrasound output value calculated by the calculating section 36a matches a setting value from the setting section 18a. The resulting judgment information is transmitted to a current value controlling section 36c by the CPU 36. The current value controlling section 36c performs fixed current control based on the judgment information so that the ultrasound output value matches the setting value.

The current value controlling section 36c is connected, for instance, to a memory 41. The memory 41 stores information such as control values used in immediately preceding control by the current value controlling section 36c. The current value controlling section 36c controls the current value with reference to information such as directly preceding control values stored in the memory 41.

For example, upon input of judgment information from the judging section 36b indicating that the detected ultrasound output value is smaller than the setting value, the current value controlling section 36c refers to the immediately preceding control value and controls the current to be larger than the immediately preceding control value.

When performing current control, the current value controlling section 36c controls a multiplication value of the multiplier 32 to compensate for the difference resulting from the comparison between the ultrasound output value and the setting value.

The calculating section 36a has a function for detecting (calculating) a mechanical impedance which includes the loaded state corresponding to when the ultrasound transducer 23 is being driven (i.e. the state in which ultrasound vibration energy is being applied to the living body tissue targeted for excision from the treatment portion 9). In other words, the calculating section 36a detects (calculates) the ultrasound (load) impedance.

The current value controlling section 36c also controls the amplitude and velocity of the vibrations to keep the vibration velocity Vus of the ultrasound in the treatment portion 9 to a predetermined range (i.e. a range appropriate for dissection and coagulation). In other words, the current value controlling section 36c functions to control vibration velocity.

By keeping the vibration velocity Vus of the ultrasound in the treatment portion 9 where the treatment is actually being performed within a predetermined range, it is possible to perform the dissection and coagulation treatment smoothly while preventing the living body tissue from sticking to the treatment portion 9.

Note that the vibration velocity Vus described here is a value at the position for performing dissection and coagulation treatment on the living body tissue targeted for treatment. Specifically, the vibration velocity Vus is controlled so that 2.3 m/s<Vus<5 m/s.

In the present embodiment, the amplitude and the like of the ultrasound vibrations are controlled so that actually the vibration velocity Vus is of an appropriate value, even when the type of the hand-piece 2, the characteristics of the ultrasound transducer 23, and the frequency of the ultrasound vibrations vary. When the ultrasound frequency has been decided, control of the vibration velocity Vus is performed by controlling the vibration amplitude.

Information for keeping the vibration velocity Vus within the predetermined range is, for instance, stored in the memory 41. The current value controlling section 36c then controls the vibration velocity Vus to within the predetermined range by referring to the stored information and controlling the amplitude of the ultrasound vibration.

As shown in FIG. 3, the instruction operation signals resulting from switching operations on the dissection selection switch 12a, the coagulation selection switch 12b and the simultaneous output switch 12c are inputted to the CPU 36. The CPU 36 then performs control corresponding to the instruction operation signal.

For instance, when the operator switches on the dissection selection switch 12a, the CPU 36 transmits the instruction operation signal to the CPU 56 of the radio-frequency wave generator 4 via the communication cable 15 and, via the CPU 56, causes output of a sinusoidal radio-frequency output signal as a continuous wave for dissection.

When the operator switches on the coagulation selection switch 12b, the CPU 36 transmits the instruction operation signal to the CPU 56 of the radio-frequency wave generator 4 via the communication cable 15, and via the CPU 56, causes output of an intermittent coagulation wave, which is a burst-wave radio-frequency output signal. When the operator switches on the simultaneous output switch 12c, the CPU 36 controls the power circuit 35 to switch on the ultrasound drive signal and, via the communication cable 15 and the CPU 56 of the radio-frequency wave generator 4, switches on the radio-frequency output.

The radio-frequency wave generator 4 includes a wave-form generating circuit 51 for generating sinusoidal and burst waves, and the signal outputted from the wave-form generating circuit 51 is inputted to an amplifier 53 via a resonating circuit 52.

The signal amplified by the amplifier 53 is applied to a primary coil side of an output transformer 54 to generate a radio-frequency output signal for ablation on a secondary coil side.

One end of the secondary coil of the output transformer 54 is connected and conducted to the horn 27 or the like which forms the conducting portion in the hand-piece 2. The other end of the secondary coil is connected and conducted to the opposing electrode plate 5 which contacts a patient 40 over a wide area.

Further, the resonating circuit 52 is supplied with a power voltage from a variable voltage power circuit 55. The wave-form generating circuit 51 and the power circuit 55 are controlled by the CPU 56.

In the present embodiment, the operator is also able to preset, by operations on a setting section 19a provided on the front panel 19, the radio-frequency output signal outputted during the simultaneous output of the ultrasound and the radio-frequency wave to a burst wave for coagulation with an intermittent wave-form. It is, of course, also possible to operate the coagulation selection switch 12b and output the burst wave as a coagulation wave.

Figure 4:
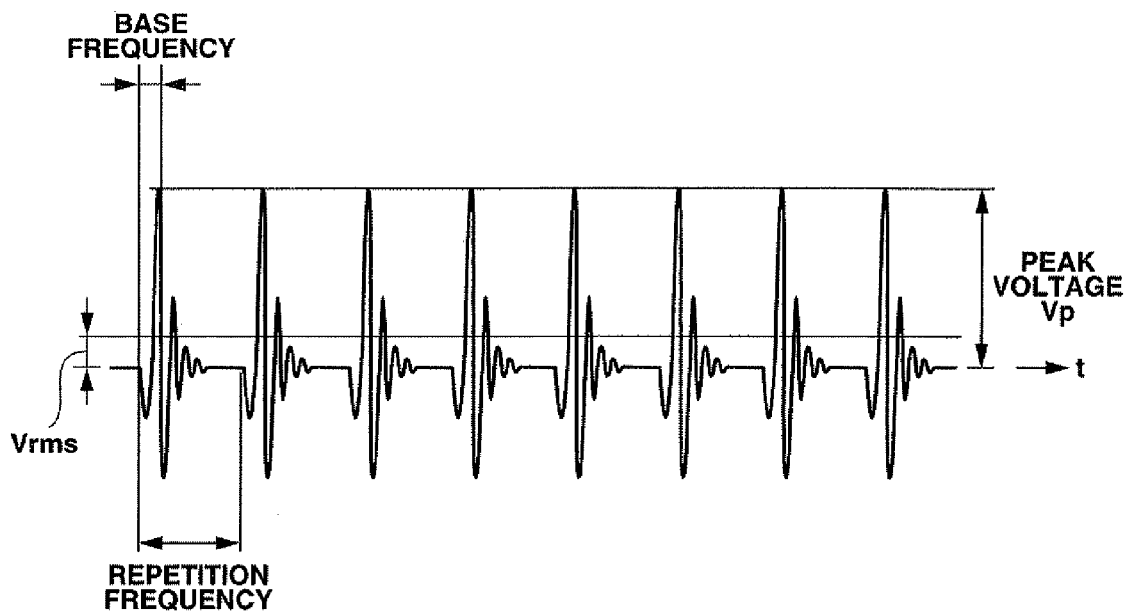
FIG. 4 is a chart of a burst wave radio-frequency signal.

FIG. 4 shows a voltage wave-form of a burst wave for the radio-frequency output signal. The cycle of the burst wave is formed with that of a repetition frequency which is composed of a plurality of repeated base wave-forms.

The burst wave is an intermittent wave in which the base wave has a large amplitude in the first and second cycle and a dramatically smaller amplitude from the third cycle onwards. From the fourth cycle onwards, the amplitude drops to near-zero. FIG. 4 shows a peak voltage (value) of the burst wave which is denoted by "Vp" and a root-mean-square value of the burst wave which is denoted by "Vrms".

As can be understood from FIG. 4, the crest factor of the burst wave, referred to hereinafter as "CF", which is calculated by dividing the peak value by the root-mean-square value is comparatively large.

As shown in FIG. 3, the operator can set a power setting value and the like of the radio-frequency wave by making settings on the setting section 19a.

A controlling section 56a of the CPU 56 controls the wave-form generating circuit 51 and the power circuit 55 according to the power setting value and the like from the setting section 19a.

When the dissection selection switch 12a has been switched on by the operator, the controlling section 56a of the CPU 56 causes the wave-form generating circuit 51 to output a sinusoidal wave as a dissection wave.

When the coagulation selection switch 12b is switched on, the controlling section 56a causes the wave-form generating circuit 51 to output a burst wave as a coagulation wave.

Note that the control information and the like from the controlling section 56a of the CPU 56 and the like are displayed on a display section 19b of the front panel 19.

Note also that, in the present embodiment, when the radio-frequency wave and the ultrasound are outputted simultaneously, the radio-frequency wave generator 4 makes use of an output mode which is used mainly for outputting a burst wave and a mixed wave produced by mixing (blending) a sinusoidal wave with the burst wave in a manner described later.

The signal amplified using the above-described amplifier 53 is inputted to a voltage detecting circuit 57a and a current detecting circuit 57b which form a detecting section 57.

The voltage detecting circuit 57a and the current detecting circuit 57b detect (measure) the voltage and current of signals amplified using the amplifier 53. The detected voltage and current are converted to digital voltage and current values by the A/D converters 58a and 58b and inputted to the CPU 56.

The CPU 56 calculates (detects) the impedance of the living body tissue (also referred to as "tissue impedance") in the calculating section 56b using the inputted voltage and current. The calculating section 56b outputs the calculated impedance value to a judging section 56c.

The judging section 56c judges whether or not the inputted impedance value falls within a fatty-tissue impedance range by comparing the inputted impedance value with a threshold impedance. In order to perform the judgment, the judging section 56c refers to fatty-tissue impedance information (specifically the threshold value) stored in a memory 59.

The CPU 56 also includes a peak detecting section 56d for detecting a peak value from the digital voltage value inputted from the voltage detecting circuit 57a via the A/D converter 58a. The peak value detected by the peak detecting section 56d is transmitted to the controlling section 56a via the judging section 56c.

When the judging section 56e judges, from the impedance value, that the tissue is fatty tissue, (at least one of) the voltage value and CF are controlled via the controlling section 56a so that that the peak value of the radio-frequency output signal does not exceed a predetermined value.

Note that the controlling section 56a may perform the functions of both the controlling section 56a and the judging section 56c in FIG. 3.

Figure 5:
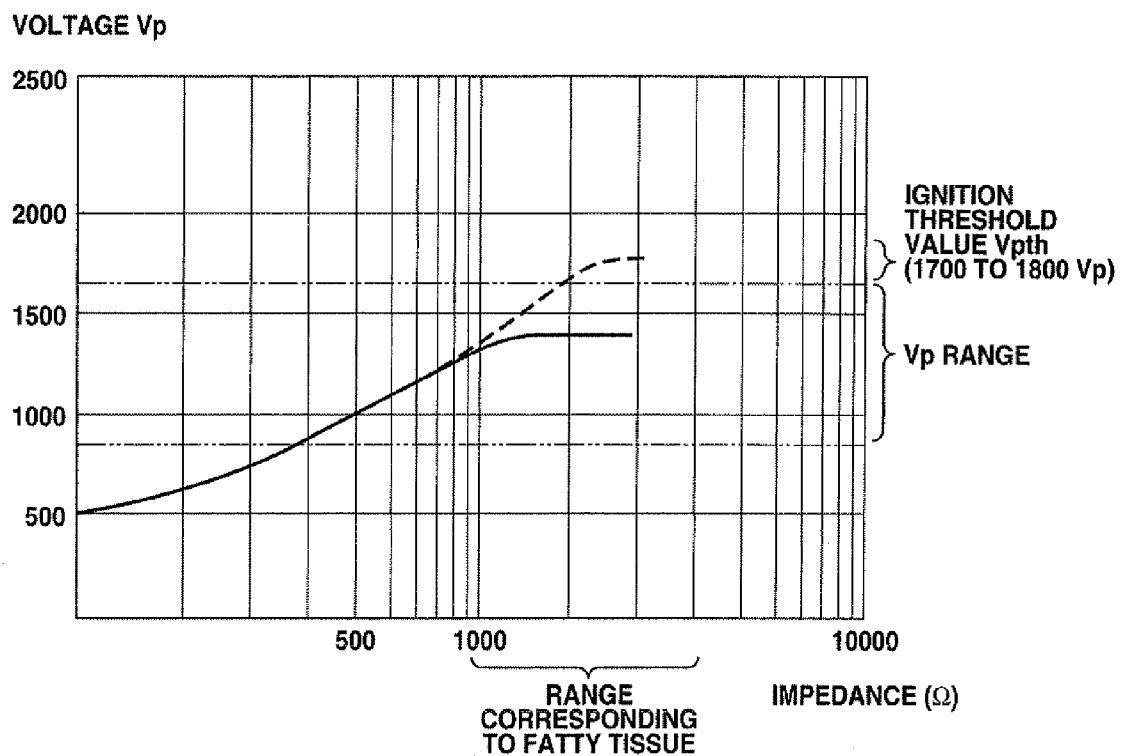
FIG. 5 is a chart for explaining the way in which a peak value of the radio-frequency output signal is limited for a range of impedance corresponding to fatty tissue.

FIG. 5 shows an example, according to the present embodiment, of control for suppressing the peak value of the radio-frequency output signal for the case in which the tissue is fatty, tissue.

In FIG. 5, the horizontal axis indicates the impedance ($\Omega$) of the living body tissue and the vertical axis indicates the peak value Vp of the voltage of the radio-frequency output signal during radio-frequency ablation.

When the impedance value is within 800$\Omega$ to 5000$\Omega$, which is a range including a small margin beyond the range of impedance values (900$\Omega$ to 4000$\Omega$) corresponding to fatty tissue, the peak value of the radio-frequency output signal is controlled to prevent a mist of fatty tissue (also referred to as a fatty mist) being ignited by sparks caused by the radio-frequency output signal. The peak value is therefore controlled to fall within a range (Vp range in FIG. 5) not exceeding a threshold value Vpth above which ignition can occur.

Note that FIG. 5 shows a case in which the range of the peak value Vp of the radio-frequency output signal is defined so that the peak value Vp is less than or equal to the threshold value Vpth of approximately 1700 V indicated by the dot-dash line, and greater than or equal to for instance, approximately 800 V to ensure that coagulation can be realized.

Thus, in the present embodiment, when the living body tissue targeted for treatment is judged to be fatty tissue by the judging section 56c, the controlling section 56a controls the output voltage of the power circuit 55 according to the judgment result.

In short, the controlling section 56a controls the root-mean-square value (Vrms) to be below a predetermined value so that the peak value of the radio-frequency output signal does not exceed the threshold value Vpth, limiting (controlling), in other words, the peak value to be within a range in which it is possible to prevent the fatty-tissue mist being ignited by the radio-frequency output signal.

With this type of control, it is possible, when the living body tissue targeted for treatment is fatty tissue, to control the peak value to be less than or equal to the threshold value Vpth, as shown by the radio-frequency control characteristic example indicated with a solid line in FIG. 5. Note that the dotted curve in FIG. 5 shows a characteristic example for the case in which such control is not performed.

With this type of control, the present embodiment makes it possible to perform treatments such as coagulation and dissection (excision) smoothly while preemptively preventing the occurrence of flames caused by the ignition of the fatty mist produced when the fatty tissue is treated.

Besides the control using the root-mean-square value by the controlling section 56a, it is also possible to employ a controlling mode for control using the CF value (described in a later section).

Note that the CPU 56 also receives input of an ON/OFF signal from the foot-switch 6. When an instruction operation for simultaneous output is performed on the foot-switch 6, ultrasound and radio-frequency waves are outputted simultaneously.

A procedure for excision of an organ 61 serving as the living body tissue of the patient 40 using the ultrasound and radio-frequency wave surgical system 1 of the above-described configuration is described below with reference to FIG. 6.

The operator connects the hand-piece 2 to the ultrasound generator 3 and the radio-frequency wave generator 4 as shown in FIG. 1.

The operator switches on the power of the ultrasound generator 3 and the radio-frequency wave generator 4. The operator then sets the output settings as shown in step S1. For example, the operator may set the ultrasound and radio-frequency output settings. The operator may, for instance, select a coagulation mode for ensuring sufficient coagulation as the radio-frequency output wave-form mode.

As shown in the schematic of FIG. 3, the operator positions the treatment portion 9 at the distal end of the hand-piece 2 on the organ 61 targeted for the excision treatment. The operator then switches on the simultaneous output switch 12c of the hand-switch 11 as indicated in step S2 in FIG. 4.

When the simultaneous output switch 12c is switched on, the resulting instruction operation signal is transmitted to the CPU 36 of the ultrasound generator 3 and, further, from the CPU 36 to the CPU 56 of the radio-frequency wave generator 4.

The CPU 36 then begins ultrasound output as indicated in step S3. The CPU 56 of the radio-frequency wave generator 4 then begins radio-frequency output of the burst wave as indicated in step S4.

As indicated in step S3, when the ultrasound output begins, the ultrasound is transmitted to the treatment portion 9 by the probe 8, and the treatment portion 9 begins ultrasound vibration.

As indicated in step S5, the current value controlling section 36c which forms part of the CPU 36 of the ultrasound generator 3 controls the current to the setting value and controls the vibration velocity Vus of the ultrasound at the treatment portion 9 to within a predetermined range.

By performing control in this way, the sticking of living body tissue to the treatment portion 9 can be reduced.

Meanwhile, as indicated in step S4, the radio-frequency wave generator 4 begins radio-frequency output of burst waves to ensure coagulation. As a result, radio-frequency waves are supplied to the treatment portion 9 and the living body tissue undergoes radio-frequency ablation, thereby beginning dissection with simultaneous blood coagulation.

Next, in step S6, when the treatment has begun, the calculating section 56b of the CPU 56 of the radio-frequency wave generator 4 begins detecting (measuring) the tissue impedance Z.

Then, in step S7, the judging section 56c judges whether or not the detected tissue impedance Z corresponds to fatty tissue. Specifically, the judging section 56c judges whether or not the calculated tissue impedance Z is between 800Ω and 5000Ω, which is the impedance range corresponding to the fatty tissue (i.e. 800Ω<Z<5000Ω). Note that 800Ω is a lower-limit threshold value and 5000Ω is an upper-limit threshold value.

When judging that the tissue impedance Z is between 800Ω and 5000Ω, the judging section 56c transmits the judgment result to the controlling section 56a.

Then, in step S8, the controlling section 56a controls the root-mean-square value (Vrms) of the radio-frequency wave so that the peak value Vp does not exceed 1700 V in the case of fatty tissue (simplified to 1700 Vp below).

As a result of such control, it is possible to prevent the fatty mist from igniting due to radio-frequency sparks during the treatment.

On the other hand, when the tissue impedance Z is judged to be outside the 800Ω and 5000Ω range (i.e. when the tissue targeted for treatment is judged not to be fatty tissue), default output characteristics are maintained as indicated in step S9.

After step S8 and step S9, the continuous radio-frequency output of step S10 is maintained. The procedure then proceeds to step S11 in which the CPU 36 judges whether the simultaneous output switch 12c of the hand-switch 11 has been switched off.

When the simultaneous output switch 12c of the hand-switch 11 has not been switched off, the procedure returns to the processing step S3 and step S4.

When, on the other hand, the simultaneous output switch 12c of the hand-switch 11 has been switched off the simultaneous output of the ultrasound and the radio-frequency waves is stopped in step S12. The treatment shown in FIG. 6 then ends.

Figure 6:
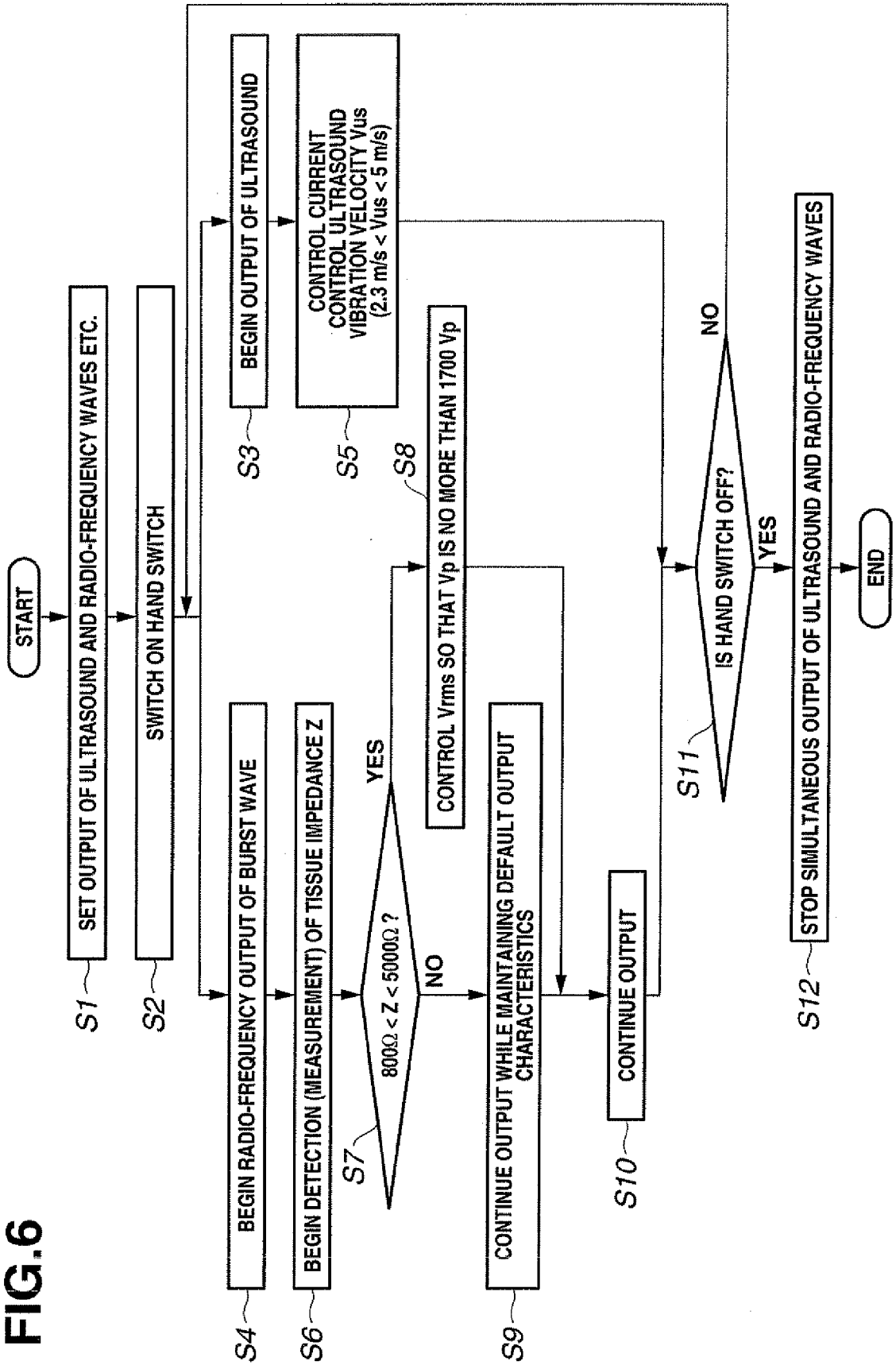
FIG. 6 is a flowchart showing an example of a processing procedure for a surgical method according to the first embodiment.
Figure 7:
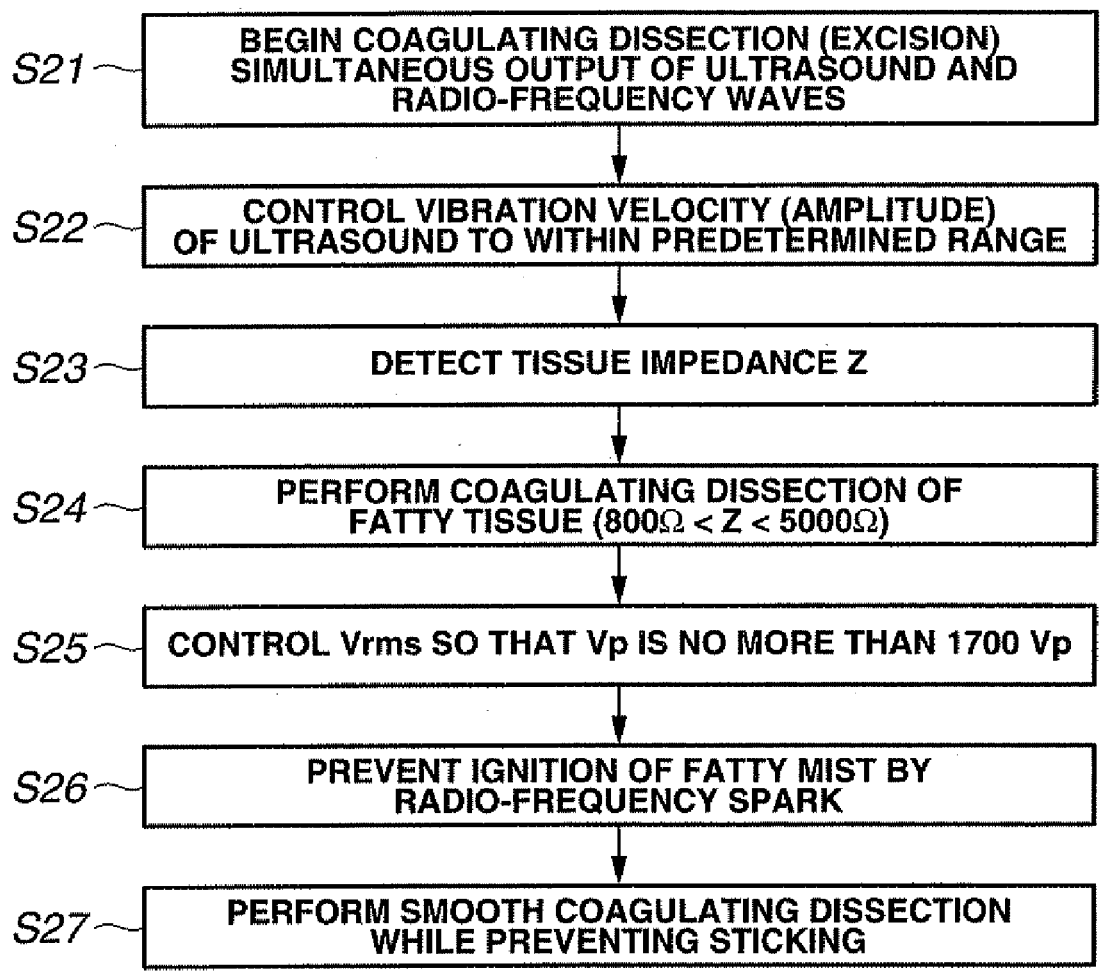
FIG. 7 is flowchart summarizing the functional processing procedure in FIG. 6.

According to surgical method shown in FIG. 6, it is possible to prevent the fatty mist produced when fatty tissue is treated from igniting due to radio-frequency sparks, allowing the operator to perform the coagulating dissection treatment smoothly. The functions of the surgical method or treatment method shown in FIG. 6 can be summarized as shown in FIG. 7. First, in step S21, the ultrasound and radio-frequency waves are outputted simultaneously to begin the coagulating dissection (excision).

Next, in step S22, the CPU 36 of the ultrasound generator 3 controls the vibration velocity (or the amplitude if the frequency is fixed) of the ultrasound vibration to within a predetermined range. Then, in step S23, the CPU 56 of the radio-frequency wave generator 4 detects the tissue impedance Z. Next, in step S24, the CPU 56 judges whether the tissue undergoing coagulating dissection is fatty tissue (i.e. judges whether 800Ω<Z<5000Ω).

When the tissue is fatty tissue, the CPU 56 controls, in step S25, the root-mean-square value (Vrms) so that Vp does not exceed 1700 Vp.

Then, as a result of the control of step S25, ignition of the fatty mist due to radio-frequency sparks during the treatment is prevented, as indicated in step S26.

Further, as a result of the control of step S22, sticking is prevented to allow smooth coagulating dissection, as indicated in S27.

Figure 8:
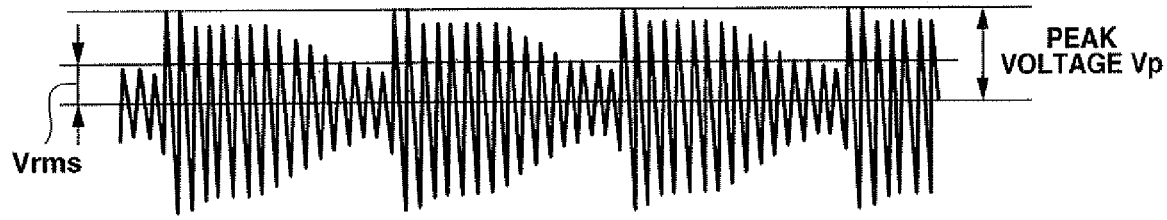
FIG. 8 is a chart showing the radio-frequency wave signal of a mixed wave.

The above-described embodiment describes an example in which, when the radio-frequency output signal is a burst wave with a large CF such as the burst wave shown in FIG. 4, the root-mean-square value is controlled so that the peak value does not exceed 1700 Vp as indicated in step S8 of FIG. 6. However, instead of controlling the root-mean-square value, a mixed wave with a smaller CF may be used as shown in FIG. 8.

The mixed wave is formed by mixing the burst wave shown in FIG. 4 and a sinusoidal wave of the type used as dissection wave. Due to the continuous sinusoidal component of the mixed wave, the root-mean-square value denoted by Vrms is larger than when the effectively intermittent burst wave is used alone.

The CF value of the mixed wave, which is calculated by dividing the peak value Vp by the root-mean-square value Vrms, is smaller (lower) than the CF value of the burst wave shown in FIG. 4.

When the mixed wave is used, the root-mean-square value Vrms is controlled to be from 550 V to 1100 V (abbreviated to 550 to 1100 Vrms) so that Vp does not exceed 1700 V in order to prevent ignition.

Thus, when the mixed wave is used in this way, it remains possible to prevent ignition in fatty living body tissue of high impedance, and perform coagulating dissection smoothly.

In the above-described example, the root-mean-square value is controlled to prevent ignition, but the CF may be controlled instead.

Figure 9:
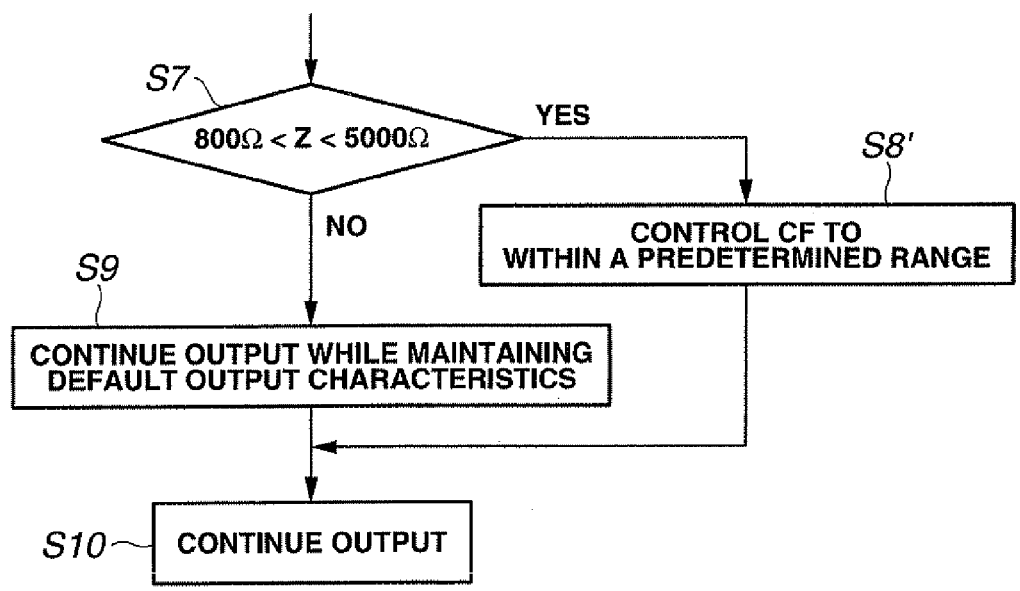
FIG. 9 is a flowchart showing a part of a control method which differs from the procedure in FIG. 6.

Specifically, the CF may be controlled so that the peak value Vp is less that 1700 V by performing, in place of step S8 in the method of FIG. 5, step S8' which limits the CF as indicated in the modification example of FIG. 9.

When the burst wave shown in FIG. 4 is used, step S8' performs control to limit the CF to a range of 3 to 7.5.

When, on the other hand, the mixed wave shown in FIG. 8 is used, step S8' performs to limit the CF to a range of 2 to 3.

By performing such control, it is possible to prevent or reduce the incidence of ignition and sticking and smoothly perform coagulating dissection treatment.

Further, control which combines step S8 and step S8' may be performed. Specifically, when the burst wave shown in FIG. 4 is used, the CF is controlled to be from 3 to 7.5, and the root-mean-square value Vrms is controlled to be from 240 V to 550 V.

When the mixed wave shown in FIG. 8 is used, the CF is controlled to be from 1.5 to 3, and the root-mean-square value Vrms is controlled to be from 550 V to 1100 V.

Second Embodiment

FIGS. 10 to 14 are for explaining a second embodiment of the invention. An overall configuration of an ultrasound and radio-frequency wave surgical system 1B of the second embodiment of the invention is substantially the same as that shown in FIG. 1. Moreover, a hand-piece 2 of the second embodiment is substantially the same as the hand-piece 2 of FIG. 2.

Figure 10:
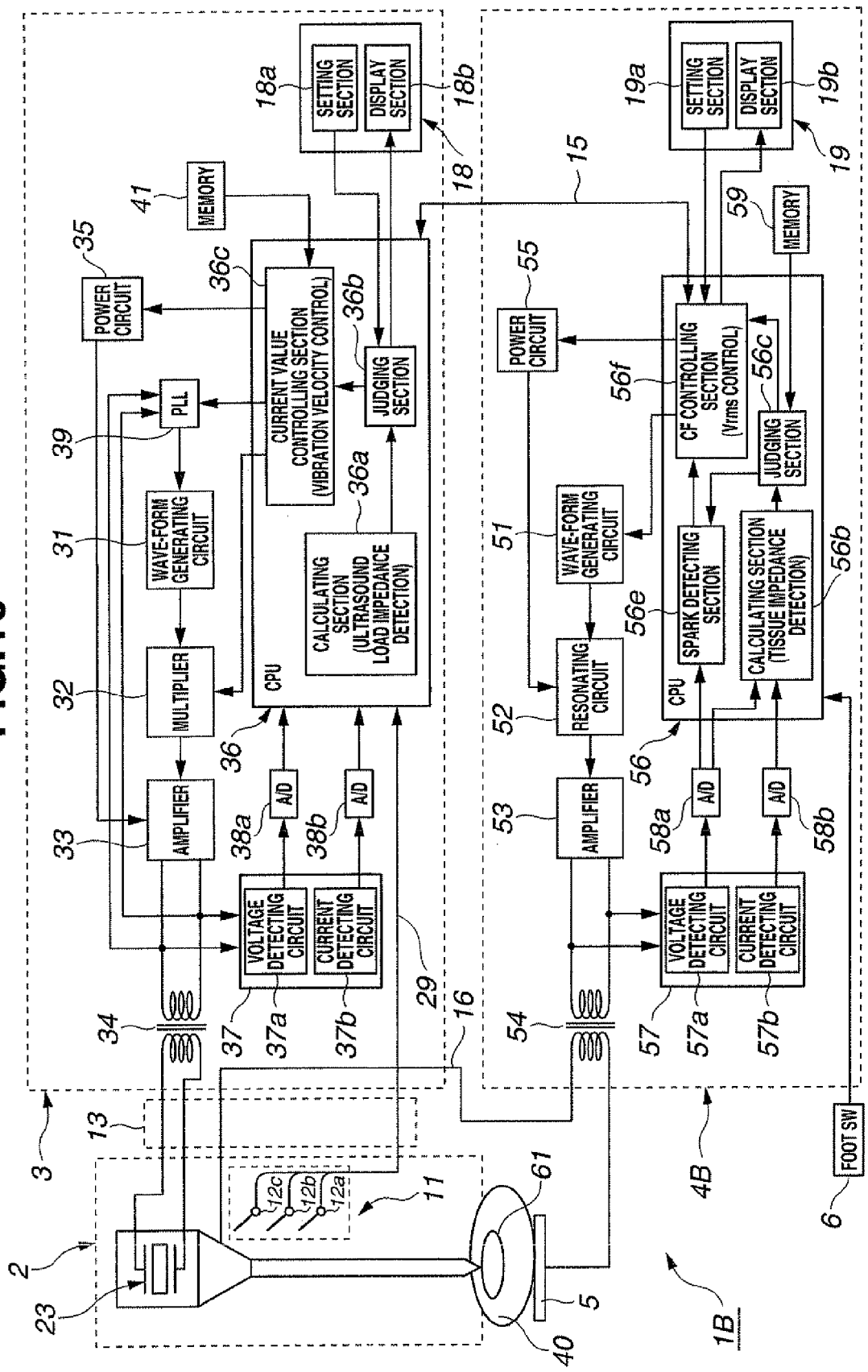
FIG. 10 is a block diagram showing a configuration of an ultrasound and radio-frequency wave surgical system of a second embodiment of the invention.

FIG. 10 shows a detailed configuration of the ultrasound and radio-frequency wave surgical system 1B of the present embodiment. The ultrasound and radio-frequency wave surgical system 1B has a similar configuration to the ultrasound and radio-frequency wave surgical system 1 of FIG. 3 except in that a radio-frequency wave generator 4B includes a spark detecting section 56e in place of the peak detecting section 56d and a CF controlling section 56f in place of the controlling section 56a in the CPU 56 of the radio-frequency wave generator 4.

The spark detecting section 56e monitors the voltage waveform of the radio-frequency wave to detect a state which immediately precedes the generation of sparks (pre-generation state). Then, when the pre-generation state is detected, the spark detecting section 56e outputs a detection signal to the CF controlling section 56f. Based on the detection signal, the CF controlling section 56f performs control to lower the CF and to lower root-mean-square value Vrms of the output voltage so as to suppress the generation of sparks, thereby preemptively preventing sparks.

In the present embodiment, the judging section 56c judges whether or not the tissue is fatty tissue using the impedance detection by the calculating section 56b in the same way as in the first embodiment However, the result of the judgment is outputted to a direct current component detecting section 62 (see FIG. 11) of the spark detecting section 56e.

Figure 11:
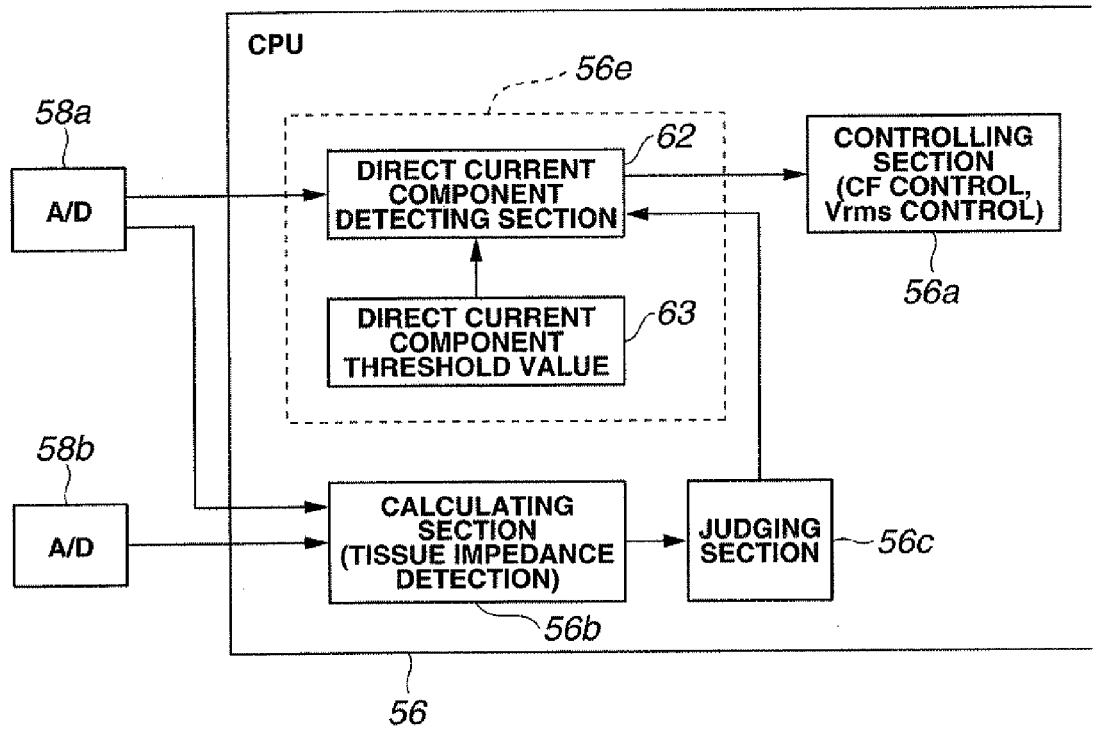
FIG. 11 is a block diagram showing a configuration of a spark detecting section.

FIG. 11 shows the configuration of the spark detecting section 56e. The spark detecting section 56e includes the direct current component detecting section 62 for detecting a direct current component from the voltage data of the A/D converter 58a and a direct current component threshold value storing section (simply denoted as "direct current component threshold value" in FIG. 11) 63 which stores a direct current component threshold value as data for judging whether or not the detected direct current component indicates the spark pre-generation state.

When the tissue has been judged to be fatty tissue by the judging section 56c, the direct current component detecting section 62 which forms part of the spark detecting section 56e detects whether or not the direct current component indicates the pre-generation state. Then, as described above, the CF controlling section 56f performs control to lower the CF and lower Vrms and thereby preemptively prevent generation of sparks depending on the result of detection of the pre-generation state.

Figure 12:
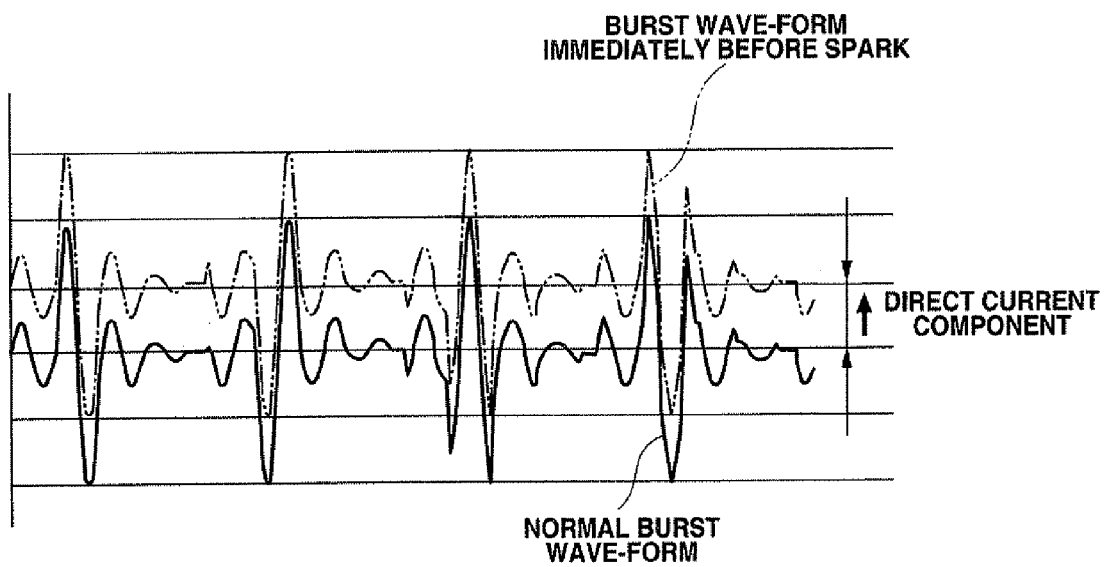
FIG. 12 is a chart of a normal burst wave-form and a burst wave-form immediately preceding the occurrence of sparks for describing operations of spark detection.

FIG. 12 is a chart for explaining operations of the spark detecting section 56e. In FIG. 12, the solid line indicates the normal burst (voltage) wave-form, and the two-dot-dash line indicates the burst wave-form immediately preceding spark generation.

As shown in FIG. 12, a direct current offset is generated in the burst wave-form immediately before spark generation. That is, normal burst wave-forms have no direct current offset and so the direct current component of such waves is "0", but the burst wave-form which immediately precedes spark generation shows a shift away from zero in the direct current component. Hence, it is possible to judge whether the spark generation is imminent by detecting whether or not the direct current component value (more accurately the absolute value) in the burst wave-form has reached a given threshold value. In the present embodiment, a direct current component threshold value is used to detect whether or not spark generation is imminent.

Figure 13:
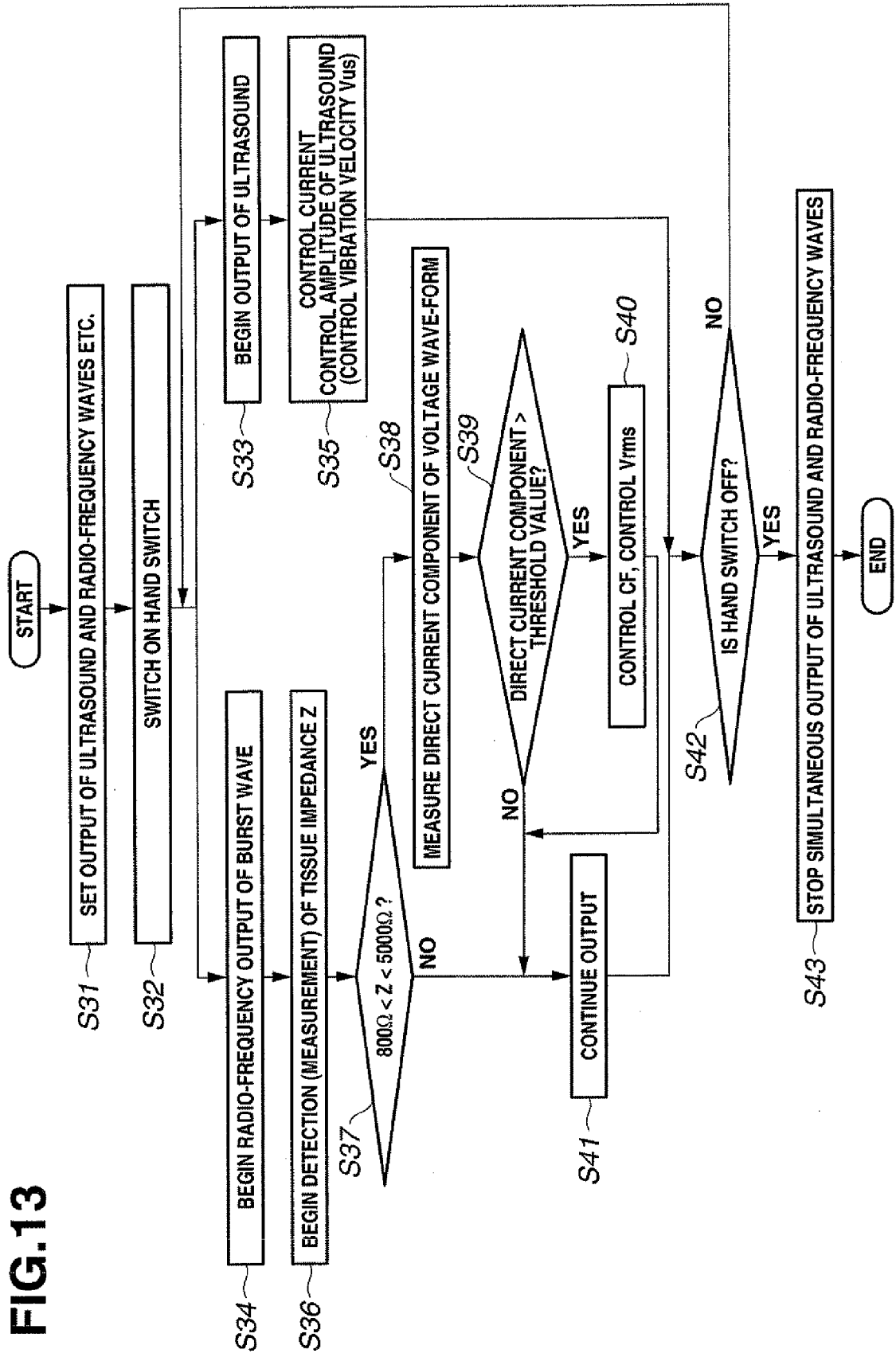
FIG. 13 is a flowchart showing an example of a processing procedure for a surgical method according to the second embodiment of the invention.

The following describes an example of the surgical method of the present embodiment with reference to FIG. 13. The operator switches on the power of the ultrasound generator 3 and the radio-frequency wave generator 4B in the same way as in FIG. 6. The operator then sets the output settings as indicated in step S31.

The operator then switches on the simultaneous output switch 12c of the hand-switch 11 as indicated in step S32.

When the simultaneous output switch 12c is switched on, the resulting instruction operation signal is transmitted to the CPU 36 of the ultrasound generator 3 and, further, from the CPU 36 to the CPU 56 of the radio-frequency wave generator 4B.

Then, the CPU 36 begins the ultrasound output as indicated in step S33. Further, the CPU 56 of the radio-frequency wave generator 411 begins radio-frequency output of the burst wave as indicated in step S34.

As a result of beginning of the ultrasound output in step S33, the ultrasound is supplied to the treatment portion 9, and the treatment portion begins ultrasound vibration.

Then, as indicated in step S35, the current value controlling section 36c which forms part of the CPU 36 of the ultrasound generator 3 performs fixed current control and controls the amplitude (vibration velocity Vus) of the ultrasound in the treatment portion 9 to be within a predetermined range.

By performing control in this way, the sticking of living body tissue to the treatment portion 9 can be reduced.

Meanwhile, as indicated in step S34, the radio-frequency wave generator 4B begins radio-frequency output of burst waves to ensure coagulation. As a result, radio-frequency waves are supplied to the treatment portion 9 and the living body tissue undergoes radio-frequency ablation, thereby beginning dissection with simultaneous blood coagulation.

Then, in step S36 when the treatment has begun, the calculating section 56b of the CPU 56 of the radio-frequency wave generator 4B begins detection (measurement) of the tissue impedance Z.

Then, in step S37, the judging section 56c judges whether or not the calculated tissue impedance Z corresponds to fatty tissue. Specifically, the judging section 56c judges whether or not the calculated tissue impedance Z is between 800Ω and 5000Ω, which is the impedance range corresponding to the fatty tissue.

When judging that the tissue impedance Z is between 800Ω and 5000Ω, the judging section 56c transmits the judgment result to the direct current component detecting section 62 of the spark detecting section 56e. Then, in step S38, the spark detecting section 56e detects (measures) the direct current component of the voltage wave-form.

Next, in step S39, the spark detecting section 56e judges whether or not the value of the detected direct current component is larger than the direct current component threshold value (referred to simply as "threshold value" in FIG. 13) stored in the direct current component threshold value storing section, When the direct current component value is judged to exceed the direct current component threshold value, the controlling section 56a performs, in step S40, control of the CF and control of Vrms so that the peak value does not exceed 1700 Vp. After the preemptive prevention of spark generation in step S40, the procedure proceeds to step S41.

Step S41 indicates that the radio-frequency output is continued in the same state as before step S41.

When, on the other hand, the detected direct current component value is judged not to exceed the direct current component threshold value in step S39, the procedure proceeds to step S41 without performing the control of step S40. After step S41, the CPU 36 judges in step S42 whether or not the simultaneous output switch 12c of the hand-switch 11 has been switched off.

When the simultaneous output switch 12c has not been switched off, the procedure returns to the processing of step S23 and step S34.

On the other hand, when the simultaneous output switch 12c has been switched off, the procedure stops the simultaneous output of the ultrasound and the radio-frequency waves in step S43, and the processing of FIG. 13 ends.

Figure 14:
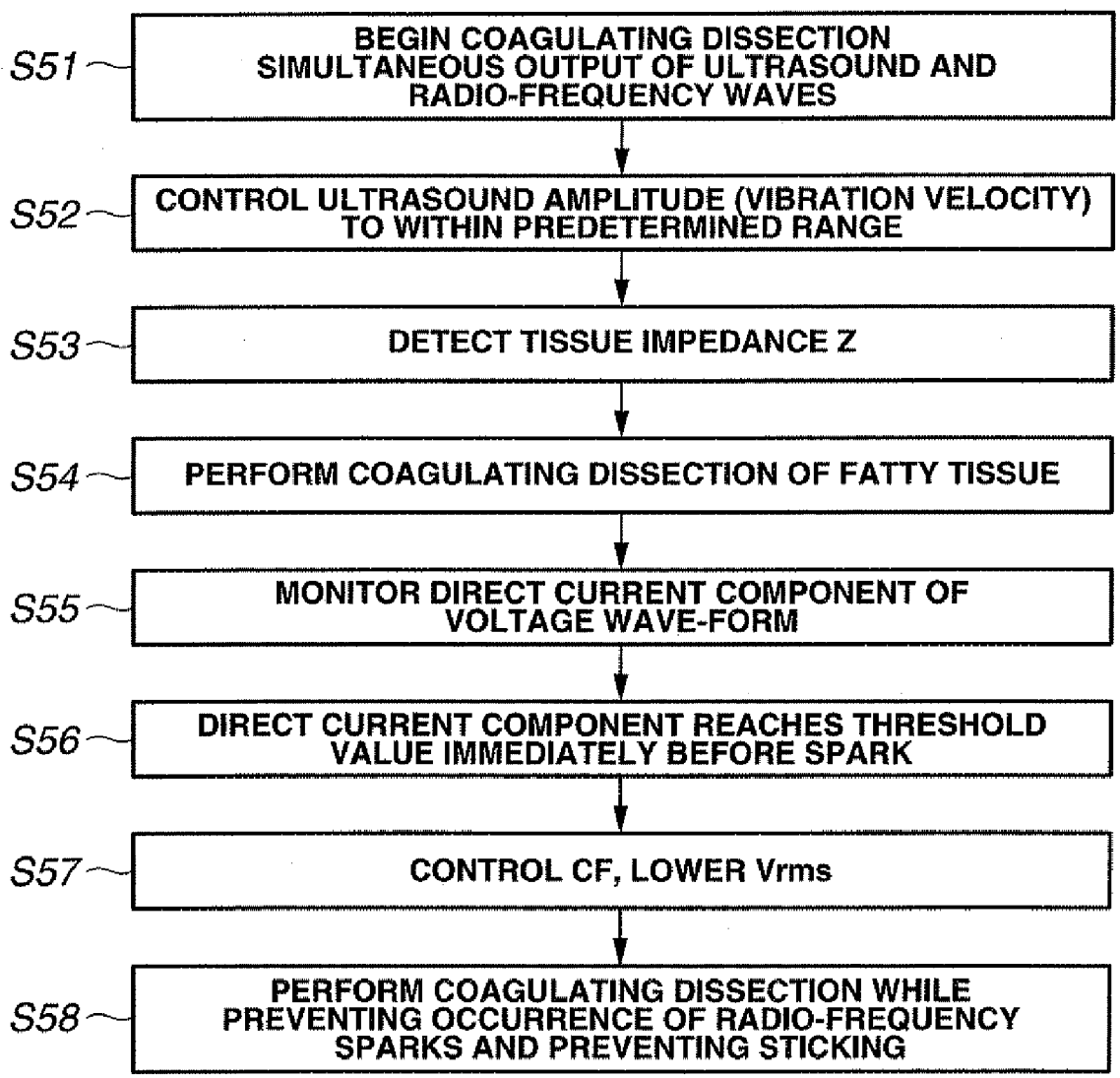
FIG. 14 is a flowchart summarizing the functional processing procedure of FIG. 13.

The functions of the surgical method or treatment method shown in FIG. 13 can be summarized as shown in FIG. 14. First, in step S51, the ultrasound and radio-frequency waves are outputted simultaneously to begin the coagulating dissection (excision). Next, in step S52, the CPU 36 of the ultrasound generator 3 controls the amplitude (or vibration velocity) of the ultrasound to within a predetermined range. Then, in step S53, the CPU 56 of the radio-frequency wave generator 413 detects the tissue impedance Z. Next, in step S54, the CPU 56 judges whether the tissue undergoing coagulating dissection is fatty tissue.

Then, in step S55, the spark detecting section 56e monitors the direct current component of the voltage wave-form. As indicated in step S56, when spark generation is imminent, the direct current component equals or exceeds the threshold value.

Thus, when a direct current component equal to or exceeding the threshold value is detected, the CPU 56 controls the CF and reduces Vrms in step S57.

Then, as indicated in step S58, the coagulating dissection is performed while preemptively preventing the generation of radio-frequency sparks and preventing sticking.

Thus, when fat is included in the living body tissue targeted for treatment, the present embodiment monitors the waveform of the radio-frequency output and, when the direct current component of the monitored wave-form is equal to or exceeds the threshold value, controls the CF of the radio-frequency output and root-mean-square voltage value to prevent ignition of the fatty tissue.

Hence, it is possible to prevent the occurrence of ignition, and smoothly perform treatments such as coagulating dissection.

Third Embodiment

The following describes a third embodiment of the invention with reference to FIGS. 15A to 18C.

An external appearance of an ultrasound and radio-frequency wave surgical system 1C of the third embodiment is the same as that of the ultrasound and radio-frequency wave surgical system 1 shown in FIG. 1. A hand-piece 2C of the present embodiment has a configuration which is shown in FIG. 15A.

Figure 15A:
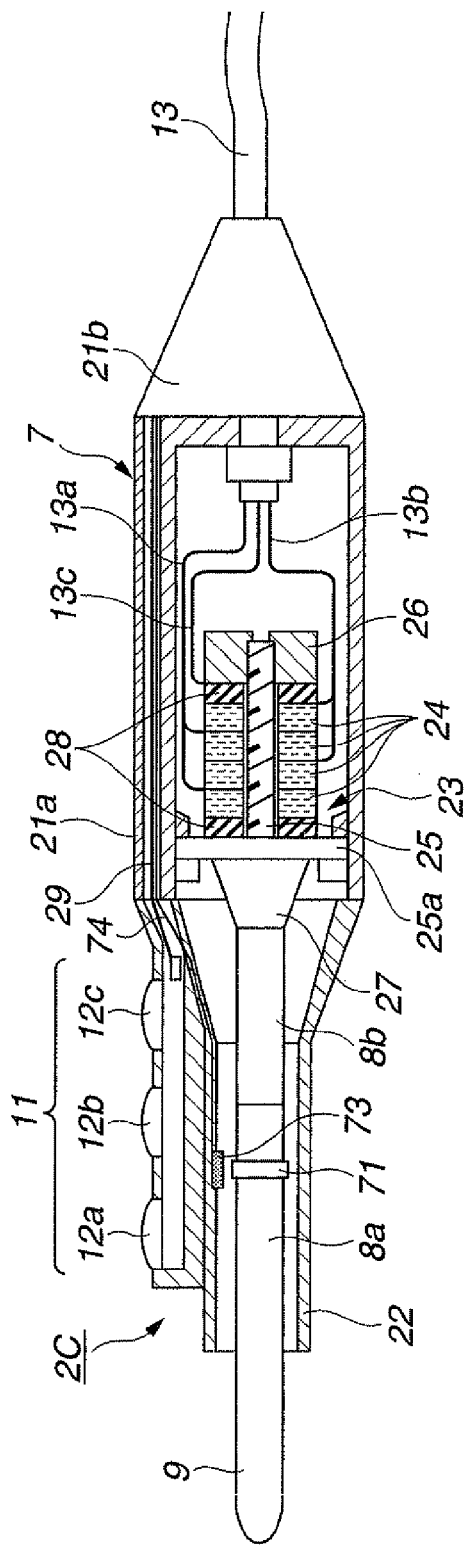
FIG. 15A and FIG. 15B are diagrams showing a configuration of a hand-piece of a third embodiment of the invention.
Figure 15B:
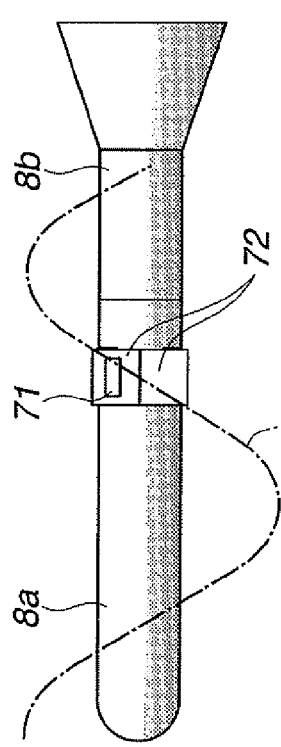

The hand-piece 2C shown in FIG. 15A is configured to be fitted with a treatment portion 9C with a different shape in the hand-piece 2 of FIG. 2, with a distal side portion of the probe 8 (hereinafter referred to as a probe distal end portion 8a) being removable. FIG. 15B shows an enlargement of the probe.

In short, in the probe 8, the probe distal end portion 8a which includes the treatment portion 9C can be removably attached to a connecting portion at the distal end of a body portion 8b including the proximal end of the probe 8. A discrimination device 71 to enable identification/discrimination of the probe distal end portion 8a (and the shape of the treatment portion 9C in particular) fixed at a proximal end portion of the probe distal end portion 8a via a discrimination device protection member 72.

Note that, as shown in FIG. 15B, the connecting portion is provided in a position which is a node when the probe 8 is caused to vibrate by the ultrasound.

Further, as shown in FIG. 15A, a sensor 73 for non-contact identification/discrimination of the discrimination device 71 is provided on the sheath 22 in a position surrounding the discrimination device 71.

Discrimination information from the sensing of the discrimination device 71 by the sensor 73 is transmitted to the CPU 36 (see FIG. 16) via a signal wire 74 which passes through the signal cable 13.

Figure 16:
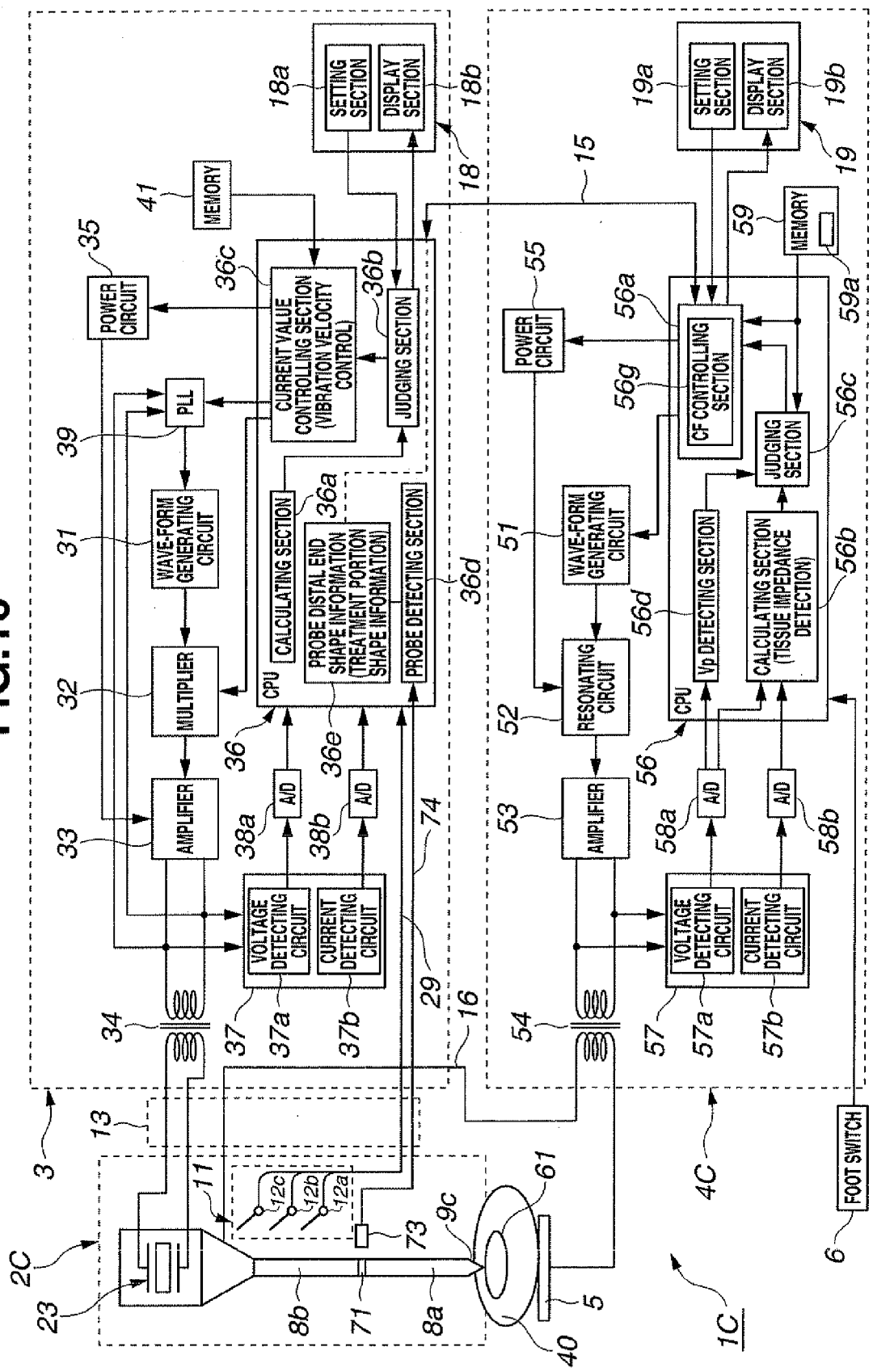
FIG. 16 is a block diagram showing a configuration of an ultrasound and radio-frequency wave surgical system of the third embodiment of the invention.

FIG. 16 shows a detailed configuration of the ultrasound and radio-frequency wave surgical system 1C of the present embodiment. The ultrasound and radio-frequency wave surgical system 1C is similar to the ultrasound and radio-frequency wave surgical system 1 of FIG. 3, but includes the hand-piece 2C in place of the hand-piece 2.

Further, in the present embodiment, the CPU 36 which receives input of the discrimination information includes a probe detecting section 36*d*.

The probe detecting section 36*d* reads treatment portion shape information as probe distal end shape information by using a lookup table (LUT) 36*e*, for example, configured with the discrimination information as address information. More specifically, the probe detecting section 36*d* reads out the shape (type) of the treatment portion which may be a hook, a ball, a blade or the like.

The LUT 36*e* contains pre-stored discrimination information and, in correspondence with the discrimination information, the treatment portion shape information.

The CPU 36 transmits the read treatment portion shape information via the communication cable 15 to the CPU 56 of the radio-frequency wave generator 4.

The controlling section 56*a* of the CPU 56 changes the CF of the burst wave or mixed wave radio-frequency output signal according to the shape of the treatment portion 9C.

When a treatment such as coagulating dissection is being performed, the amount of mist generated mainly due to cavitation depends on the shape of the treatment portion.

Thus, in the present embodiment, when the treatment portion 9C is of a shape which makes cavitation more likely to occur, a CF controlling section 56*g* in the controlling section 56*a* performs control to lower the CF in order to suppress the generation of the mist.

When, on the other hand, the treatment portion 9C is of a shape which allows a reduction in cavitation, the CF controlling section 56*g* controls the CF to be larger than the above-described CF.

Thus, the memory 59, for instance has stored therein a CF value 59*a* corresponding to the distinguished treatment portion shape information, and the CF controlling section 56*g* reads out the corresponding CF value 59*a* and perform control.

Thus, in the present embodiment, the CF value 59*a* of the radio-frequency output signal is changed according to the shape of the attached treatment portion 9C which is actually attached.

Note that the controlling section 56*a* performs the control of the CF and the root-mean-square value to prevent ignition in the same way as in the first embodiment.

Further, other configurations are the same as those of the first embodiment.

Figure 17:
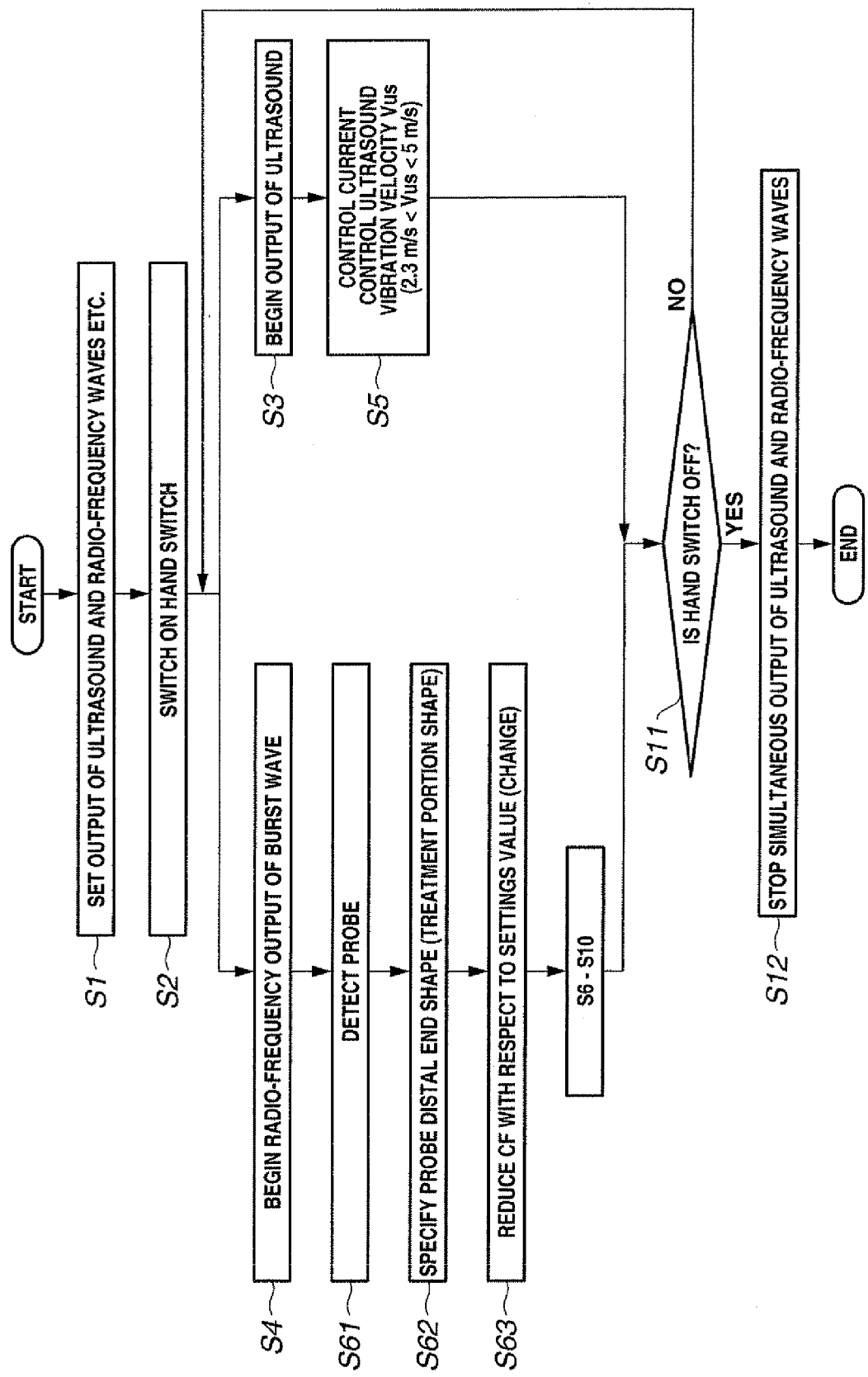
FIG. 17 is a flowchart showing an example of a processing procedure for a surgical method of the third embodiment.

The following describes operations of the present embodiment with reference to the flowchart of FIG. 17. FIG. 17 is similar to the flowchart of FIG. 6 except in that processing corresponding to steps S61 to S63 is inserted between step S4 and step S5.

In step S4, the radio-frequency output of the burst wave begins. Then, in step S61, the probe detecting section 36*e* of the CPU 36 reads the discrimination information from the sensor 73 and starts a probe detection operation.

Then, in step S62, the probe distal end shape, which is the treatment portion shape (i.e. the shape/type of the treatment portion, which may be a hook or the like), is specified using the information stored in the LUT 36*e*. The specified information is transmitted from the CPU 36 to the CPU 56.

Next, in step S63, the CF controlling section 56*g* of the CPU 56 lowers (changes) the CF with respect to radio-frequency output setting value of step S1 according to the specified treatment portion shape.

For instance, an actual radio-frequency output value may be set by multiplying the setting value by a reduction factor of 0 to 100% depending on the treatment portion shape.

After the step S63, the processing corresponding to step S6 to S10, which is shown in an abbreviated manner in FIG. 17, is performed.

According to the present embodiment, it is possible not only to obtain the advantages of the first embodiment, but also to suppress the generation of mist and prevent ignition in an effective way when different treatment portions 9C are attached and used.

More specifically, since the amount of mist generated differs when the shape of the treatment portion 9C is changed, if the control of the root-mean-square value and the CF value is performed to prevent the ignition without taking the shape of the treatment portion 9C into consideration, the accuracy of the controlling function may drop.

If, on the other hand, the generated amount of mist is controlled in a manner dependent on the shape of the treatment portion 9C so as not to be too large, it is possible to effectively prevent the occurrence of ignition by commonly controlling the root-mean-square value and the CF value.

Alternatively, the root-mean-square value and CF for preventing the occurrence of ignition when the tissue has been judged to be fatty tissue may be controlled to change according to the shape of the treatment portion 9C.

With this arrangement, when the operator exchanges the treatment portion 9C, the root-mean-square value and the CF value can be set corresponding to the fitted treatment portion 9C so that the peak value of the resulting wave-form does not exceed a value at which the occurrence of ignition can be prevented.

Other configurations are the same as those of the first embodiment. Note that the above-described hand-piece 2C may be used in the second embodiment.

Figure 18A:
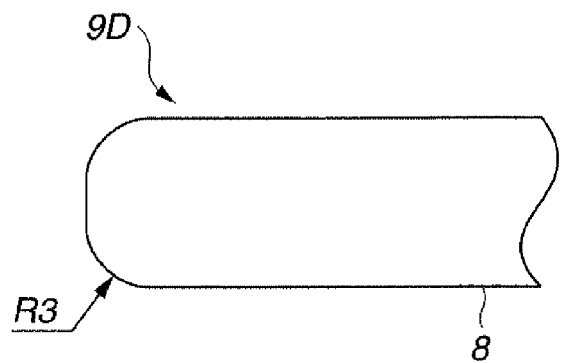
FIGS. 18A to 18C are example shapes of a treatment portion.
Figure 18B:
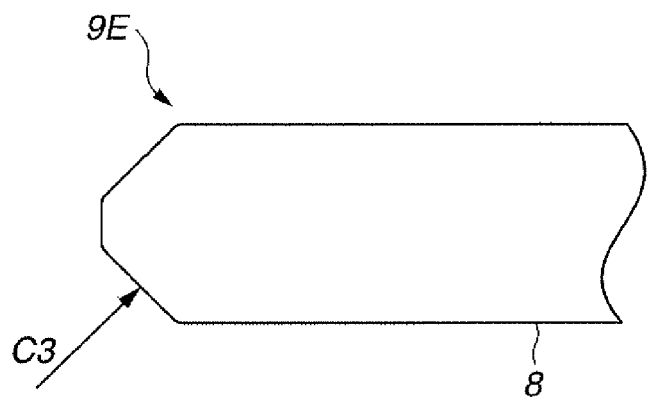
Figure 18C:
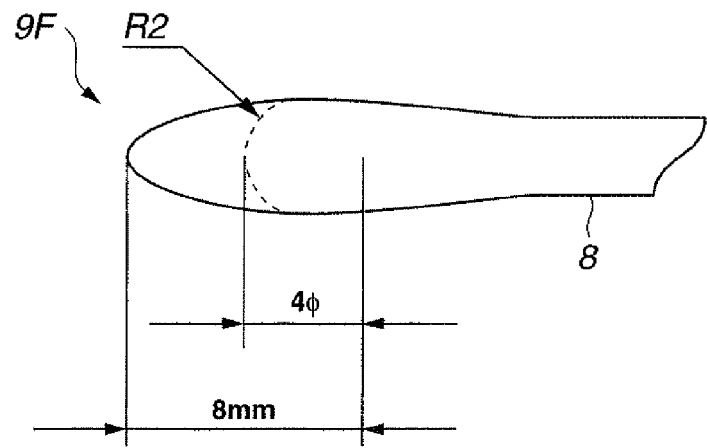

Further, the treatment portion at the distal end side of the probe 8 may, for instance, take any of the shapes shown in FIGS. 18A to 18C.

In the example shown in FIG. 18A, a treatment portion 9D at the distal end of the probe 8 is provided with a curved portion (R 0.5 to R 3) tangential to a plane perpendicular to the axis direction at the distal end of the treatment portion 9D. The curved portion covers at least 80% of the circumference of ridge plane of the treatment portion 9D.

In the example shown in FIG. 18B, a treatment portion 9E at the distal end of the probe 8 is provided with a chamfered portion (C 0.5 to C 3) starting in a plane perpendicular to the axis direction at the distal end of the treatment portion 9D. The chamfered portion covers at least 80% of the circumference of ridge plane of the treatment portion 9E.

In the example shown in FIG. 18C, a treatment portion 9F at the distal end of the probe 8 has an elliptic shape (an elongated shape with a curved surface). The elliptic shape has a length of 8 mm which is twice the diameter of the spherical shape treatment portion (diameter 4 mm).

By employing treatment instruments of the above described shapes it is possible to suppress cavitation and thereby suppress the generation of a mist.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgical system comprising:
   a treatment member that treats living body tissue targeted for treatment by applying an ultrasound vibration and a radio-frequency electrical current to the living body tissue, the treatment member provided at a distal end portion of an elongated probe;

an ultrasound transducer that generates the ultrasound vibration under application of an ultrasound drive signal, the ultrasound transducer transmitting the generated ultrasound vibration to the treatment member via the probe;

an ultrasound drive signal generator that generates the ultrasound drive signal to be applied to the ultrasound transducer;

a radio-frequency wave generator that generates a radio-frequency output signal having an output wave-form defined by a base frequency and a repetition frequency so as to supply the radio-frequency output signal to the treatment member via the probe;

a detecting circuit including a voltage detecting circuit that detects a voltage of the radio-frequency output signal applied to the living body tissue via the treatment member and an electric current detecting circuit that detects an electric current flowing through the living body tissue;

an electric impedance detecting circuit that detects and electric impedance value which the living body tissue has based on the voltage and the electric current detected by the detecting circuit;

a memory that stores a threshold value set for judging whether or not the living tissue has an electric impedance value within a range in a case where the living body tissue is fatty tissue;

a judging circuit that judges whether or not the living body tissue includes a component corresponding to the fatty tissue by comparison of the electric impedance of the living tissue targeted for treatment detected by the detecting circuit, and the threshold value stored in the memory;

a peak value detecting circuit that detects a voltage peak value of the radio-frequency output signal detected by the voltage detecting circuit; and a controller that controls the peak value of the radio-frequency output signal detected by the peak value detecting circuit not to exceed a predetermined value, if it is judged by the judging circuit that the electric impedance value detected by the electric impedance detecting circuit when the ultrasound vibration from the ultrasound transducer to the treatment member and the radio-frequency output signal from the radio-frequency wave generator to the treatment member are simultaneously supplied is an electric impedance within the range between an upper-limit threshold value and a lower-limit threshold value as the threshold value stored in the memory to be corresponding to the fatty tissue.

2. The surgical system according to claim 1, further comprising:

a vibration velocity controller including a memory device that stores information for holding a vibration velocity of the ultrasound vibration for the treatment member within a predetermined range, the vibration velocity controller controlling the vibration velocity of the ultrasound vibration to be held within the predetermined range referring to the information in the memory device.

3. The surgical system according to claim 1, wherein the treatment member is removably attached to a distal end side of a treatment instrument to be grasped by an operator;

the surgical system further comprising an identifying circuit that identifies the treatment member attached to the treatment instrument, and wherein the controller controls at least one of the voltage root-mean-square value and the crest factor according to an identification result from the identifying circuit.

4. The surgical system according to claim 1, further comprising:

a direct current component detecting circuit that detects a direct current component of the output wave-form of the radio-frequency electrical power, wherein the controller controls at least one of the voltage root-mean-square value and the crest factor based on a value of the direct current component detected by the direct current component detecting circuit.

5. The surgical system according to claim 4, wherein the controller controls at least one of the voltage root-mean-square value and the crest factor according to the impedance value detected by an impedance detecting circuit and a direct current component detected by a direct current component detecting circuit, when the radio-frequency electrical power is supplied to the living body tissue via the treatment member.

6. The surgical system according to claim 1, wherein the radio-frequency output signal defined by the base frequency and the repetition frequency is radio-frequency output signal that is a mixed wave made up of a coagulation wave and a dissection wave, and the controller controls a voltage root-mean-square value of the radio-frequency output signal and a crest factor which is calculated by dividing a voltage peak value by the voltage root-mean-square value so that the voltage root-mean-square value is in a range of 550 V to 1100 V and the crest factor is in a range of 1.5 to 3.

7. The surgical system according to claim 1, wherein the radio-frequency output signal defined by the base frequency and the repetition frequency is the radio-frequency output signal of a coagulation wave, and the controller controls a voltage root-mean-square value of the radio-frequency output signal and a crest factor which is calculated by dividing a voltage peak value by the voltage root-mean-square value so that the voltage root-mean-square value is in a range of 240 V to 550 V and the crest factor is in a range of 3 to 7.5.

8. The surgical system according to claim 1, wherein the controller controls at least one of the voltage root-mean-square value and the crest factor so that the voltage peak value is maintained within a range an upper limit of 1700 V if the electric impedance value detected by the electric impedance detecting circuit when the radio-frequency output signal is supplied to the living body tissue via the treatment member is in a range between the lower-limit threshold value of 800Ω and the upper-limit threshold value of 5000Ω.

9. The surgical system according to claim 2, wherein the vibration velocity controller controls an amplitude of the vibration velocity so that the vibration velocity is within a range of 2.3 m/s to 5 m/s.

10. The surgical system according to claim 1, including a controller that performs control to supply the ultrasound vibration and the radio-frequency output signal simultaneously to the treatment member and control to stop the supply.

11. The surgical system according to claim 1, wherein the treatment member is provided in a treatment instrument including the ultrasound transducer and the probe for transmitting the ultrasound vibration to the treatment member.

12. The surgical system according to claim 1, wherein the controller comprises a voltage root-mean-square value controller that controls a voltage root-mean-square voltage root-mean-square value of the radio-frequency output signal and a crest factor controller that controls a crest factor which is calculated by dividing the voltage peak value by the voltage root-mean-square value.

13. The surgical system according to claim 1, wherein the controller comprises a voltage root-mean-square value controller that controls a voltage root-mean-square value of the radio-frequency output signal and a crest factor controller that controls a crest factor which is calculated by dividing the voltage peak value by the voltage root-mean-square value.

* * * * *

UNITED STATES PATENT AND TRADEMARK OFFICE
CERTIFICATE OF CORRECTION

PATENT NO. : 8,308,721 B2  
APPLICATION NO. : 12/327982  
DATED : November 13, 2012  
INVENTOR(S) : Norikiyo Shibata et al.

Page 1 of 1

It is certified that error appears in the above-identified patent and that said Letters Patent is hereby corrected as shown below:

In the Claims

It Should Read:

Column 17, line 24 (claim 1, line 23): an electric impedance detecting circuit that detects an Column 19, line 7 (claim 12, line 2): controller comprises at least one of the voltage root-mean-square value con- Column 19, lines 8-9 (claim 12, lines 3-4): troller that controls a voltage root-mean-square value of the radio-frequency output signal and a Signed and Sealed this  
Ninth Day of April, 2013

Teresa Stanek Rea  
*Acting Director of the United States Patent and Trademark Office*